US008263670B2

(12) United States Patent
Acosta et al.

(10) Patent No.: US 8,263,670 B2
(45) Date of Patent: Sep. 11, 2012

(54) MIXED FLUOROALKYL-ALKYL SURFACTANTS

(75) Inventors: Erick Jose Acosta, New Castle, DE (US); Charles Kenneth Taylor, Thorofare, NJ (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1002 days.

(21) Appl. No.: 11/890,414

(22) Filed: Aug. 6, 2007

(65) Prior Publication Data

US 2009/0038510 A1    Feb. 12, 2009

(51) Int. Cl.
*B01D 12/00* (2006.01)
*B01F 17/14* (2006.01)
*C09D 5/00* (2006.01)
*C09D 7/06* (2006.01)
*C09D 7/12* (2006.01)
*C07F 9/09* (2006.01)
*C09K 3/18* (2006.01)
*C11D 1/34* (2006.01)
*C08L 21/02* (2006.01)
*C09D 201/00* (2006.01)

(52) U.S. Cl. ............ 516/199; 588/188; 588/70; 588/90; 588/113; 588/175; 588/183; 588/186; 106/2; 106/18.31; 252/8.61; 510/467; 524/144; 427/412; 427/412.4

(58) Field of Classification Search .................. 516/199; 558/70, 186, 188, 90, 113, 175, 183; 106/2, 106/18.31; 252/8.61; 510/467; 524/144; 427/412, 412.4

See application file for complete search history.

(56) References Cited

U.S. PATENT DOCUMENTS

| | | | |
|---|---|---|---|
| 3,083,224 A | | 3/1963 | Brace et al. |
| 3,692,885 A * | | 9/1972 | Anello et al. ................. 558/186 |
| 3,839,254 A | | 10/1974 | Fang |
| 3,880,798 A * | | 4/1975 | Deem et al. ................... 523/200 |
| 3,911,056 A * | | 10/1975 | Houghton ..................... 558/175 |
| 3,979,469 A | | 9/1976 | Jäger |
| 4,145,382 A | | 3/1979 | Hayashi et al. |
| 5,481,028 A | | 1/1996 | Petrov et al. |
| 5,674,934 A | | 10/1997 | Schmidt et al. |
| 6,184,187 B1 * | | 2/2001 | Howell et al. ................. 508/427 |
| 6,271,289 B1 | | 8/2001 | Longoria et al. |
| 6,461,998 B2 * | | 10/2002 | Lenti et al. .................... 508/182 |
| 6,506,806 B2 | | 1/2003 | Taylor et al. |
| 6,684,525 B2 * | | 2/2004 | DeSimone et al. ............. 34/329 |
| 7,470,818 B2 * | | 12/2008 | Peng et al. ........................ 568/8 |
| 7,553,985 B2 * | | 6/2009 | Shtarov et al. ................ 558/204 |
| 7,674,928 B2 * | | 3/2010 | Peng et al. ...................... 558/86 |
| 7,728,163 B2 * | | 6/2010 | Taylor et al. .................. 558/204 |
| 8,022,238 B2 * | | 9/2011 | Peng et al. ..................... 558/169 |
| 2001/0031709 A1 * | | 10/2001 | Lenti et al. .................... 508/182 |
| 2005/0107645 A1 | | 5/2005 | Furukawa |
| 2006/0148671 A1 | | 7/2006 | Dams et al. |
| 2007/0049646 A1 | | 3/2007 | Moore et al. |
| 2008/0108785 A1 * | | 5/2008 | Jackson et al. ................ 528/401 |
| 2009/0042996 A1 * | | 2/2009 | Taylor et al. .................. 514/785 |
| 2010/0267843 A1 * | | 10/2010 | Taylor et al. .................. 514/772 |

FOREIGN PATENT DOCUMENTS

| | | |
|---|---|---|
| DE | 20 38 890 A1 | 2/1971 |
| JP | 2002 196459 A | 2/1971 |
| WO | WO 95/11877 | 5/1995 |
| WO | WO 02/26921 A1 | 4/2002 |
| WO | 2008/060352 A1 | 5/2008 |

OTHER PUBLICATIONS

Guo et al., Hybrid Surfactants Containing Separate Hydrocarbon and Fluorocarbon Chains; Journal of Physical Chemistry (1992), 96(16), 6738-42.
Guo et al., Exchange of Hybrid Surfactant Molecules Between Monomers and Micelles; Journal of Physical Chemistry (1992), 96(24), 10068-74.
Yoshino et al., Syntheses of Hybrid Anionic Surfactants Containing Fluorocarbon and Hydrocarbon Chains; Langmuir (1995), 11(2), 466-9.
Balague et al., Synthesis of fluorinated telomers, Part 1, Telomerization of vinylidene fluoride with perfluoroalkyl iodides; J. of Fluorine Chemistry (1995) 70(2) 215-223.
Miyazawa et al., Synthesis of Phosphate-Type Fluorocarbon-Hydrocarbon Hybrid Surfactants and Their Adsorption onto Calcium Hydroxyapatite; Journal of Fluorine Chemistry (2005), 126(3), 301-306.
Inoue et al., Micelle Formation of Phosphate-type Hybrid Surfactants in Aqueous Solution; Journal of Oleo Science (2005), 54(2), 95-103.
Hoda, et al., Langmuir monolayer properties of the fluorinated-hydrogenated hybrid amphiphiles with dipalmitoylphosphatidylcholine (DPPC); Colloids and Surfaces B: Biointerfaces 47 (2006) 165-175.
Timperley, et al., Fluorinated phosphorus compounds Part 6. The synthesis of bis(fluoroalkyl) phosphites and bis(fluoroalkyl) phosphorohalidates; Journal of Fluorine Chemistry 113 (2002) 65-78.
Keiper et al, "Self-Assembly of Phosphate Fluorosurfactants in Carbon Dioxide", Langmuir, vol. 20, 2004, pp. 1065-1072, XP002499490, compounds 5-10, Abstract, published on the web Jan. 16, 2004.
Keiper et al, "New Phosphate Fluorosurfactants for Carbon Dioxide", J. Am. Chem. Soc., vol. 124, No. 9, 2002, pp. 1834-1835, XP002499301, compound 2, figures 1-3.

* cited by examiner

*Primary Examiner* — Daniel S Metzmaier

(57) ABSTRACT

A compound of Formula 1

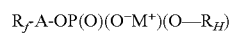

Formula 1 wherein
$R_f$ is a $C_2$ to $C_6$ linear or branched perfluoroalkyl optionally interrupted by one, two or three ether oxygen atoms;
A is $(CH_2CF_2)_m(CH_2)_n$—, $(CH_2)_oSO_2N(CH_3)(CH_2)_p$—, $O(CF_2)_q(CH_2)_r$—, or $OCHFCF_2OE$-;
m is 1 to 4; n, o, p, and r are each independently 2 to 20; q is 2;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
M is a Group I metal or an ammonium cation $(NH_xR^2_y)^+$ wherein $R^2$ is a $C_1$ to $C_4$ alkyl, x is 1 to 4, y is 0 to 3 and x+y is 4; and
$R_H$ is a $C_1$ to $C_{20}$ linear, branched, or cyclic alkyl, or a $C_6$ to $C_{10}$ aryl, and its use as a surfactant is disclosed.

14 Claims, No Drawings

MIXED FLUOROALKYL-ALKYL SURFACTANTS

FIELD OF INVENTION

The field of invention is related to the synthesis and use of fluorochemical surfactants.

BACKGROUND OF INVENTION

For surfactants and surface treatment agents with fluorochemical chains, longer perfluoroalkyl chains contain a higher percentage of fluorine at a given concentration and typically provide better performance. However, the fluorinated materials derived from longer perfluoroalkyl chains are more expensive. Reduction of the fluorine content with delivery of the same or higher performance is therefore desirable. Reducing the fluorine content would reduce the cost, but it is necessary to maintain product performance.

Desimone et al., in WO 02/26921, described hybrid phosphates of the structure $R_fO-PO(OR_H)(O^-M^+)$ wherein $R_f$ is $C_nF_{(2n+1)}(CH_2)_m$, $R_H$ is $C_nH_{(2n+1)}$, or $C_nF_{(2n+1)}(CH_2)_m$, n and m are 1 to 24, and $M^+$ is $K^+$, $Na^+$, or $NH_4^+$. Desimone et al. described the use of these compounds as surfactants for use in liquid carbon dioxide, but not as surfactants in water or other media.

It is desirable to improve surfactant performance, in particular lowering of surface tension in aqueous systems, and to increase the fluorine efficiency, i.e., boost the efficiency or performance of the surfactants so a lower proportion of the expensive fluorine component is required to achieve the same level of performance, or to have better performance using the same level of fluorine. Especially desirable would be surfactants having similar or superior performance in aqueous systems compared to current commercial products but having shorter perfluoroalkyl groups. The present invention provides such surfactants.

SUMMARY OF THE INVENTION

The present invention comprises a compound of Formula 1

$$R_f\text{-A-OP(O)(O}^-M^+)(O-R_H) \qquad \text{Formula 1}$$

wherein $R_f$ is a $C_2$ to $C_6$ linear or branched perfluoroalkyl optionally interrupted by one, two or three ether oxygen atoms;

A is $(CH_2CF_2)_m(CH_2)_n-$, $(CH_2)_oSO_2N(CH_3)(CH_2)_p-$, $O(CF_2)_q(CH_2)_r-$, or $OCHFCF_2OE-$;

m is 1 to 4; n, o, p, and r are each independently 2 to 20; q is 2;

E is a $C_2$ to $C_{20}$ linear or branched alkyl group optionally interrupted by oxygen, sulfur, or nitrogen atoms; a cyclic alkyl group, or a $C_6$ to $C_{10}$ aryl group;

M is a Group I metal or an ammonium cation $(NH_xR^2_y)^+$ wherein $R^2$ is a $C_1$ to $C_4$ alkyl, x is 1 to 4, y is 0 to 3 and x+y is 4; and $R_H$ is a $C_1$ to $C_{20}$ linear, branched, or cyclic alkyl, or a $C_6$ to $C_{10}$ aryl.

The present invention further comprises a method of lowering the surface tension of an aqueous medium comprising contacting the medium with a composition of Formula 1 as defined above.

The present invention further comprises a method of providing leveling, open time extension, and resistance to blocking to a coated substrate comprising adding to a coating base prior to deposition on the substrate a compound of Formula 1 as defined above.

The present invention further comprises a substrate treated with the above method.

DETAILED DESCRIPTION

Trademarks are shown herein in upper case.

Herein the term "twin-tailed surfactant" is used to describe a surfactant having two hydrophobic groups attached to a single connecting hydrophilic group. The two hydrophobic groups may be the same, designated as "symmetrical twin-tailed surfactant", or dissimilar, designated as "hybrid twin-tailed surfactant".

The present invention comprises a fluoroalkylalkyl compound of Formula 1

$$R_f\text{-A-OP(O)(O}^-M^+)(O-R_H) \qquad \text{Formula 1}$$

wherein

A is $(CH_2CF_2)_m(CH_2)_n-$, $(CH_2)_oSO_2N(CH_3)(CH_2)_p-$, $O(CF_2)_q(CH_2)_r-$, or $OCHFCF_2OE-$;

$R_f$ is a $C_2$ to $C_6$ linear or branched perfluoroalkyl optionally interrupted by one, two or three ether oxygen atoms;

$R_H$ is a $C_1$ to $C_{20}$ linear, branched, or cyclic alkyl, or a $C_6$ to $C_{10}$ aryl; and M is a Group I metal or an ammonium cation $(NH_xR^2_y)^+$ wherein $R^2$ is a $C_1$ to $C_4$ alkyl, x is 1 to 4, y is 0 to 3 and x+y is 4;

m is 1 to 4; n, o, p, and r are each independently 2 to 20, and q is 2.

E is a $C_2$ to $C_{20}$ linear or branched alkyl group optionally interrupted by oxygen, sulfur, or nitrogen atoms; a cyclic alkyl group, or a $C_6$ to $C_{10}$ aryl group.

Formula 1 is a hybrid twin-tailed surfactant. The compounds of Formula 1 are prepared according to the method described by Longoria et al in U.S. Pat. No. 6,271,289, and Brace and Mackenzie, in U.S. Pat. No. 3,083,224. Typically, either phosphorus pentoxide ($P_2O_5$) or phosphorus oxychloride ($POCl_3$) is reacted with fluoroalkyl alcohol or fluoroalkyl thiol to give mixtures of the mono- and bis(fluoroalkyl)phosphoric acids. Neutralization, using common bases such as ammonium or sodium hydroxides, or alkanol amines, for instance, diethanolamine (DEA), provides the corresponding phosphates. Reacting an excess of fluoroalkyl alcohol or fluoroalkyl thiol with $P_2O_5$ followed by neutralization provides a mixture of mono(fluoroalkyl)phosphate and bis(fluoroalkyl)phosphate. Higher ratios of bis(fluoroalkyl)phosphate to mono(fluoroalkyl)phosphate are obtained by using the method of Hayashi and Kawakami in U.S. Pat. No. 4,145,382. The phosphite and phosphinate compositions are prepared in a similar manner. The fluoroalkyl alcohol or fluoroalkyl thiol used as a reactant in the preparation of Formula 1 compounds are described below for various embodiments. Preferred are compounds of Formula 1 wherein $R_f$ is a $C_3$ to $C_6$ perfluoroalkyl. More preferred are those wherein $R_f$ is $C_4$ or $C_6$ perfluoroalkyl.

One embodiment of the invention is a compound of Formula 1 wherein A is $(CH_2CF_2)_m(CH_2)_n-$, herein denoted as Formula 2, $$R_f-(CH_2CF_2)_m(CH_2)_n-O-P(O)(OR^1)(O^-M^+) \qquad \text{Formula 2}$$

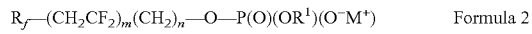

wherein $R_f$, $R^1$, m, n, and M are as defined above in Formula 1. Preferred compounds of Formula 2 include those wherein $R_f$ is a $C_4$ or $C_6$ perfluoroalkyl, and n is 2.

Fluorinated alcohols useful in the preparation of various embodiments of Formula 2 are available by synthesis according to the following scheme:

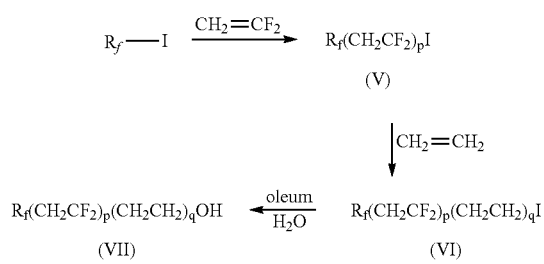

(V)

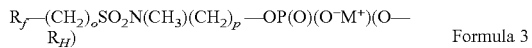

(VII)    (VI)

The telomerization of vinylidene fluoride (VDF) with linear or branched perfluoroalkyl iodides is well known, and produces compounds of the structure $R_f(CH_2CF_2)_pI$, wherein, p is 1 to 3 or more and $R_f$ is a C1 to C6 perfluoroalkyl group. For example, see Balague, et al, "Synthesis of fluorinated telomers, Part 1, Telomerization of vinylidene fluoride with perfluoroalkyl iodides", J. Flour Chem. (1995), 70(2), 215-23. The specific telomer iodides (V) are isolated by fractional distillation. The telomer iodides (V) can be treated with ethylene by procedures described in U.S. Pat. No. 3,979,469, (Ciba-Geigy, 1976) to provide the telomer ethylene iodides (VI) wherein q is 1 to 3 or more. The telomer ethylene iodides (VI) can be treated with oleum and hydrolyzed to provide the corresponding telomer alcohols (VII) according to procedures disclosed in WO 95/11877 (Elf Atochem S. A.). The higher homologs (q=2, 3) of telomer ethylene iodides (VI) are available with excess ethylene at high pressure. The telomer ethylene iodides (VI) can be treated with a variety of reagents to provide the corresponding thiols according to procedures described in J. Fluorine Chemistry, 104, 2 173-183 (2000). One example is the reaction of the telomer ethylene iodides (VI) with sodium thioacetate, followed by hydrolysis.

A further embodiment of the invention is a compound of Formula 1 wherein A is $(CH_2)_oSO_2N(CH_3)(CH_2)_p$—, herein denoted as Formula 3, $$R_f\text{—}(CH_2)_oSO_2N(CH_3)(CH_2)_p\text{—}OP(O)(O^-M^+)(O\text{—}R_H)$$    Formula 3 wherein $R_f$, $R_H$, o, p, and M are as defined above in Formula 1. Preferred compounds of Formula 3 include those wherein o and p are each 2, $R_f$ is $C_6$ perfluoroalkyl and $R_H$ is $C_8H_{17}$. The fluoroalkyl alcohol used to prepare compounds of Formula 3 is available from E. I. du Pont de Nemours and Company, Wilmington Del.

A further embodiment of the invention is a compound of Formula 1 wherein A is $O(CF_2)_q(CH_2)_r$—, herein denoted as Formula 4, $$R_f\text{—}O(CF_2)_q(CH_2)_r\text{—}OP(O)(O^-M^+)(O\text{—}R_H)$$    Formula 4 wherein $R_f$, $R_H$, q, r, and M are as defined above in Formula 1. Preferred compounds of Formula 4 include those wherein q and r are each 2, $R_f$ is $C_3F_7$ and $R_H$ is $C_8H_{17}$.

The fluoroalcohols used as starting materials to make the compositions of Formula 4 are available by the following series of reactions:

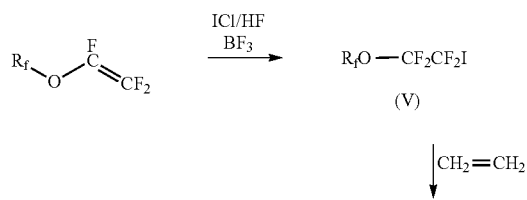

(V)

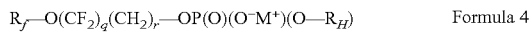

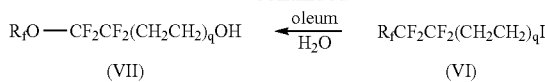

(VII)    (VI)

The starting perfluoroalkyl ether iodides of formula (V) above can be made by the procedure described in U.S. Pat. No. 5,481,028, in Example 8, which discloses the preparation of compounds of formula (V) from perfluoro-n-propyl vinyl ether.

In the second reaction above, a perfluoalkyl ether iodide (V) is reacted with an excess of ethylene at an elevated temperature and pressure. While the addition of ethylene can be carried out thermally, the use of a suitable catalyst is preferred. Preferably the catalyst is a peroxide catalyst such as benzoyl peroxide, isobutyryl peroxide, propionyl peroxide, or acetyl peroxide. More preferably the peroxide catalyst is benzoyl peroxide. The temperature of the reaction is not limited, but a temperature in the range of 110° C. to 130° C. is preferred. The reaction time can vary with the catalyst and reaction conditions, but 24 hours is usually adequate. The product is purified by any means that separates unreacted starting material from the final product, but distillation is preferred. Satisfactory yields up to 80% of theory have been obtained using about 2.7 mols of ethylene per mole of perfluoalkyl ether iodide, a temperature of 110° C. and autogenous pressure, a reaction time of 24 hours, and purifying the product by distillation.

The perfluoroalkylether ethylene iodides (VI) are treated with oleum and hydrolyzed to provide the corresponding alcohols (VII) according to procedures disclosed in WO 95/11877 (Elf Atochem S. A.). Alternatively, the perfluoroalkylether ethyl iodides can be treated with N-methyl formamide followed by ethyl alcohol/acid hydrolysis. A temperature of about 130° to 160° C. is preferred. The higher homologs (q=2, 3) of telomer ethylene iodides (VI) are available with excess ethylene at high pressure.

The telomer ethylene iodides (VI) are treated with a variety of reagents to provide the corresponding thiols according to procedures described in J. Fluorine Chemistry, 104, 2 173-183 (2000). One example is the reaction of the telomer ethylene iodides (VI) with sodium thioacetate, followed by hydrolysis. The telomer ethylene iodide (VI) can also be treated to provide the corresponding thioethanols or thioethylamines by conventional methods.

A further embodiment of the invention is a compound of Formula 1 wherein A is OCHFCF$_2$OE-, herein denoted as Formula 5, $$R_f\text{—}OCHFCF_2OE\text{-}OP(O)(O^-M^+)(O\text{—}R_H)$$    Formula 5 wherein $R_f$, $R_H$, E and M are as defined above in Formula 1. Preferred compounds of Formula 5 include those wherein $R_f$ is $C_3F_7$ and $R_H$ is $C_8H_{17}$.

The fluoroalcohols used as starting materials to make the compositions of Formula 5 are prepared by reacting a dioxane and fluorocarbon with at least one unsaturated group with a diol in the presence of an alkali metal compound. For example, a dioxane and a compound of formula $R_fOCF=CF_2$ are reacted with a diol such as $HO(CH_2)_2OH$ in the presence of an alkali metal such as KOH typically in a sealed stainless steel reaction vessel at about 70° C. for about 8 hours. Further details are provided in US Patent Application 2005/0107645.

The compositions of the present invention are surfactants for use in aqueous formulations, where extremely low surface tensions (about 18 dynes/cm=18 mN/m) are required. The surfactants of the present invention provide "fluorine efficiency". The term "fluorine efficiency" means to increase the efficiency or improve the performance of the surfactants or treating agents so a lower proportion of the expensive fluorine component is required to achieve the same level of performance, or to have better performance using the same level of fluorine. Compared with conventional fluorinated surfactants, the fluorine content in the surfactants of the present invention is from about 25 to about 36% lower than in conventional fluorinated surfactants.

While not wishing to be bound by theory, a mixture of a fluoroalkyl surfactant and a separate alkyl surfactant is often less effective in reducing the surface tension than the fluoroalkyl surfactant alone. It is believed that the more strongly hydrophobic fluoroalkyl groups preferentially displace the less strongly hydrophobic alkyl groups at the interface. However, when the fluoroalkyl and alkyl hydrophobic groups coexist together in the same molecule, the alkyl hydrophilic groups cannot be displaced, and the surfactant properties are thereby improved. Furthermore, in the surfactants of the present invention, both the fluoroalkyl and alkyl groups have a high degree of freedom of rotation, permitting unrestricted orientation at the interface. In the prior art, when fluoroalkyl/alkyl surfactants in which the fluoroalkyl group, the alkyl group, and the hydrophilic group were all bound to a single carbon atom, the tetrahedral structure for the carbon atom forced a separation in the orientation of the fluoroalkyl and alkyl groups (the bond angle is 109.5° for the H—C—H angle in the symmetrical tetrahedral methane molecule). Typically, such fluoroalkyl/alkyl surfactants in which the fluoroalkyl group, the alkyl group, and the hydrophilic group were all bound to a single carbon atom, do not show surface tension results as low as 18 mN/m. It is believed that the approximately 110° forced separation may diminish the effectiveness of the fluoroalkyl/alkyl combination in such prior art examples, compared with the structures of Formula 2 above, wherein the fluoroalkyl and alkyl groups are unrestricted in orientation and can orient essentially parallel to each other.

The present invention further comprises a method of lowering surface tension of an aqueous medium comprising contacting the medium with a composition of Formula 1 as described above. Any of a wide variety of media are suitable for use in the method of the present invention. Typically the medium is a liquid. Preferred are aqueous, hydrocarbon, and halocarbon systems. Examples of suitable medium include a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium. A low concentration of about 0.1% by weight of surfactant is sufficient to lower surface tension to less than about 24 mN/m, preferably less than about 22 nM/m. For many surfactants of the present invention concentrations of 0.01% by weight of the surfactant are effective to achieve a surface tension of less than about 22 mN/m.

The present invention further comprises a method of providing leveling, open time extension, and resistance to blocking to a coated substrate comprising adding to a coating base prior to deposition on the substrate a compound of Formula 1.

"Leveling" as used herein refers to the uniformity of coverage of the coating when applied to a substrate. It is undesirable to have streaking, surface defects, or withdrawal of the coating from the substrate surface at the edges or otherwise. An even coating will provide a superior dried coating on the substrate surface. The term "open time extension" is used herein to mean the time period during which a layer of liquid coating composition can be blended into an adjacent layer of liquid coating composition without showing a lap mark, brush mark, or other application mark. It is also called wet-edge time. Latex paints containing low boiling, volatile organic chemicals (VOC) have shorter than desired open-time due to lack of high boiling temperature VOC solvents. Lack of open time extension will cause surface defects such as overlapping brush marks or other marks. A longer open time is beneficial when the appearance of the coated surface is important, as it permits application of the coating without leaving overlap marks, brush marks, or other application marks at the area of overlap between one layer of the coating and an adjacent layer of the coating. "Blocking" is the undesirable sticking together of two coated surfaces when pressed together, or placed in contact with each other for an extended period of time, after the coating has dried. When blocking occurs separation of the surfaces can result in disruption of the coating on one or both surfaces. Thus resistance to blocking is beneficial in many situations where two coated surfaces need to be in contact, for example on window frames.

Suitable coating compositions, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. I, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

When used as additives to a coating base the compositions of the present invention of Formula 1 as defined above are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about from about 0.01 weight % to about 1 weight %, and more preferably from about 0.1 weight % to about 0.5 weight % is used.

Floor waxes, polishes, or finishes (hereinafter "floor finishes") are generally water based or solvent based polymer emulsions. The surfactants of Formula I of the present invention are suitable for use in such floor finishes. Commercially available floor finish compositions typically are aqueous emulsion-based polymer compositions comprising one or more organic solvents, plasticizers, coating aides, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly (alkyl methacrylates). Commercially available acrylic copolymers used in floor finishes include, for example, methyl methacrylate/butyl acrylate/methacrylic acid (MMA/BA/MAA) copolymers; methyl methacrylate/butyl acrylate/acrylic acid (MMA/BA/AA) copolymers, and the like. Commercially available styrene-acrylic copolymers include styrene/methyl methacrylate/butyl acrylate/methacrylic acid (S/MMA/BA/MMA) copolymers; styrenelmethyl methacrylate/butyl acrylate/acrylic acid (S/MMA/BA/AA) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenerated coconut oil or soybean oil, and the mineral waxes such as paraffin or ceresin. The waxes typically range from 0 to about 15 weight percent and preferably from about 2 to about 10 weight percent based on the weight of the finish composition.

When used as additives to a floor finish the compositions of the present invention of Formula 1 as defined above are effectively introduced to the composition by thoroughly stirring it in at room or ambient temperature. More elaborate mixing can be employed such as using a mechanical shaker or providing heat or other methods. When used as an additive to floor finishes, the compositions of the invention generally are added at about 0.001 weight % to about 5 weight % by dry weight of the composition of the invention in the wet composition. Preferably about from about 0.01 weight % to about 1 weight %, and more preferably from about 0.1 weight % to about 0.5 weight % is used.

Floor waxes or polishes are water based, solvent based and polymer. The surfactants of the present invention are suitable for use with any of these. Water-based and polymer waxes dry to a high gloss without buffing; solvent-based wax requires vigorous buffing. Water-based wax is recommended for asphalt, vinyl, vinyl asbestos and rubber-tiled floors; solvent-based waxes produce a hard, shiny finish and are best for wood, cork and terrazzo floors. Self-polishing waxes, such as polymer or resin, will yellow or discolor and wear off in heavy traffic areas; they should be stripped off and reapplied after three or four coats.

The compounds of Formula I are useful in many additional applications. Examples of some applications include use in fire fighting compositions, for example as a wetting agent, emulsifying agent and/or dispersion. They are also useful as a component in aqueous film forming extinguishing agents, and as an additive to dry chemical extinguishing agents in aerosol-type extinguishers, and as a wetting agent for sprinkler water.

The compounds of Formula I of the present invention are suitable for the use in agricultural compositions. Examples include as a wetting agent, emulsifying agent and/or dispersion agent for herbicides, fungicides, weed killers, parasiticides, insecticides, germicides, bactericides, nematocides, microbiocides, defolients, fertilizers and hormone. growth regulators. Formula I compounds are also suitable as a wetting agent for foliage, for live stock dips and to wet live stock skins; as an ingredient in sanitizing, discoloring and cleaning compositions; and in insect repellent compositions. The compounds of Formula 1 are also useful as a wetting agent, emulsifying agent and/or dispersion agent for the manufacture of paper and plywood veneer. The compounds of Formula I are also suitable for use as grease/oil repellents for paper, wood, leather, skins, metals, textiles, stone, and tiles, and as penetrant for preservative impregnation.

The compounds represented by Formula I of the present invention are also suitable for the use as a wetting agent, emulsifying agent and/or dispersion agent for polymerization reactions, particularly polymerization of fluoromonomers. These compounds are also suitable as a latex stabilizer; as an additive for foam applications to control spreading, crawling and edge buildup; as foaming agents, as mold release agents or as demolding agents; as an internal antistatic agent and antiblocking agent for polyolefins; as a flow modifier for extruding hot melts, spreading, uniformity, anticratering; and as a retarder for plasticizer migration or evaporation in the plastics and rubber industry.

The compounds of Formula I of the present invention are further suitable for the use in the petroleum industry as a wetting agent for oil well treatments, drilling mud; as a film evaporation inhibitor for gasoline, jet fuel, solvents, and hydrocarbons; as a lubricant or cutting oil improver to improve penetration times; as an oil spill collecting agent; and as additive to improve tertiary oil well recovery.

The compounds of Formula I of the present invention are further suitable for the use in textile and leather industries as a wetting agent, antifoaming agent, penetrating agent or emulsifying agent; or as a lubricant for textiles, nonwoven fabrics and leather treatment; for fiber finishes for spreading, and uniformity; as a wetting agent for dyeing; as a binder in nonwoven fabrics; and as a penetration additive for bleaches.

The compounds of Formula I of the present invention are further suitable for the use in the mining and metal working industries, in the pharmaceutical industry, automotives, building maintenance and cleaning, in household, cosmetic and personal products, and in photography and graphic arts to provide improved surface effects.

The hybrid fluoroalkyl/alkyl surfactants of the present invention provide compounds having surfactant effects at low concentrations, such as below 0.5% by weight in water. The compounds of the invention contain less fluorine (improved fluorine efficiency), have a lower surface tension or are generally comparable to conventional fluoroalkyl surfactants. Thus the inventive compositions provide the advantage of altering surface properties using less fluorine to achieve the same level of performance, or provide better performance using the same level of fluorine, as prior art compositions. Thus the improvements in the surfactant characteristics reduce overall manufacturing cost while improving the performance of the surfactant products.

Materials and Test Methods

The following materials were used in the examples herein.
1) $C_4F_9CH_2CF_2CH_2CH_2OH$ Ethylene (25 g) was introduced to an autoclave charged with $C_4F_9CH_2CF_2I$ (217 g) and d-(+)-limonene (1 g), and the reactor heated at 240° C. for 12 h. The product was isolated by vacuum distillation to provide $C_4F_9CH_2CF_2CH_2CH_2I$.

Fuming sulfuric acid (70 mL) was added slowly to 50 g of $C_4F_9CH_2CF_2CH_2CH_2I$ and mixture stirred at 60° C. for 1.5 h. The reaction was quenched with ice-cold 1.5 wt % $Na_2SO_3$ aqueous solution and heated at 95° C. for 0.5 h. The bottom layer was separated and washed with 10 wt % aqueous sodium acetate, and distilled to provide $C_4F_9CH_2CF_2CH_2CH_2OH$: bp 54~57° C. at 2 mmHg (267 Pascals).

2) $C_4F_9(CH_2CF_2)_2CH_2CH_2OH$

Ethylene (18 g) was introduced to an autoclave charged with $C_4F_9(CH_2CF_2)_2I$ (181 g) and d-(+)-limonene (1 g), and the reactor heated at 240° C. for 12 h. The product was distilled to provide $C_4F_9(CH_2CF_2)_2CH_2CH_2I$.

Then $C_4F_9(CH_2CF_2)_2CH_2CH_2I$ (10 g) and N-methylformamide (8.9 mL) were heated to 150° C. for 26 h. The reaction was cooled to 100° C., followed by the addition of water to separate the crude ester. Ethyl alcohol (3 mL) and p-toluene sulfonic acid (0.09 g) were added to the crude ester, and the reaction was stirred at 70° C. for 15 min. Then ethyl formate and ethyl alcohol were distilled out to give a crude product. The crude alcohol was dissolved in ether, washed with aqueous sodium sulfite, water, and brine in series, and dried over magnesium sulfate. The product was distilled to give $C_4F_9(CH_2CF_2)_2CH_2CH_2OH$: bp 90~94° C. at 2 mmHg Pascals).

3) $C_6F_{13}CH_2CF_2CH_2CH_2OH$

Ethylene (15 g) was introduced to an autoclave charged with $C_6F_{13}CH_2CF_2I$ (170 g) and d-(+)-limonene (1 g), and then the reactor was heated at 240° C. for 12 h. Product was isolated by vacuum distillation to provide $C_6F_{13}CH_2CF_2CH_2CH_2I$. Fuming sulfuric acid (129 mL) was added slowly to $C_6F_{13}CH_2CF_2CH_2CH_2I$ (112 g). The mixture was stirred at 60° C. for 1.5 h. Then the reaction was quenched with ice-cold 1.5 wt % aqueous $Na_2SO_3$ and heated at 95° C. for 0.5 h. The bottom layer was separated and washed with 10% sodium acetate aqueous solution and distilled to provide $C_6F_{13}CH_2CF_2CH_2CH_2OH$.: mp 38° C.

4) $C_6F_{13}(CH_2CF_2)_2CH_2CH_2OH$

Ethylene (56 g) was introduced to an autoclave charged with $C_6F_{13}(CH_2CF_2)_2I$ (714 g) and d-(+)-limonene (3.2 g), and the reactor heated at 240° C. for 12 h. Product was isolated by vacuum distillation to provide $C_6F_{13}(CH_2CF_2)_2$ CH$_2$CH$_2$I. Then C$_6$F$_{13}$(CH$_2$CF$_2$)$_2$I (111 g) and N-methylformamide (81 mL) were heated to 150° C. for 26 h. The reaction was cooled to 100° C., followed by the addition of water to separate the crude ester. Ethyl alcohol (21 mL) and p-toluene sulfonic acid (0.7 g) were added to the crude ester, and the reaction was stirred at 70° C. for 15 min. Then ethyl formate and ethyl alcohol were distilled out to give a crude alcohol. The crude alcohol was dissolved in ether, washed with aqueous sodium sulfite, water, and brine in turn, and then dried over magnesium sulfate. The product was distilled under vacuum to provide compound 12: mp 42° C.

5) C$_3$F$_7$OCF$_2$CF$_2$CH$_2$CH$_2$OH

C$_3$F$_7$OCF$_2$CF$_2$I (100 g, 0.24 mol) and benzoyl peroxide (3 g) were charged under nitrogen into a vessel. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of C$_3$F$_7$OCF$_2$CF$_2$CH$_2$CH$_2$I in 80% yield. The boiling point was 56~60° C. at 25 mm Hg pressure (3325 Pa).

A mixture of C$_3$F$_7$OCF$_2$CF$_2$CH$_2$CH$_2$I (300 g, 0.68 mol) and N-methyl-formamide (300 mL), was heated to 150° C. for 26 hours. Then the reaction was cooled to 100° C., followed by the addition of water to separate the crude ester. Ethyl alcohol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 199 g of C$_3$F$_7$OCF$_2$CF$_2$CH$_2$CH$_2$OH in 85% yield. The boiling point was 71~73° C. at 40 mmHg (5320 Pa).

6) C$_3$F$_7$OCFHCF$_2$CH$_2$CH$_2$OH

In an initial step CF$_3$CF$_2$CF$_2$OCHFCF$_2$OCH$_2$CH$_2$OCH$_2$Ph was prepared as follows. In a dry box, a 500 mL Pyrex bottle was charged with 2-(Benzyloxy)ethanol (98%, Aldrich Chemical Company) (40.0g, 0.263 mole) and 130 mL of anhydrous dimethylformamide (Aldrich SURE/SEAL). NaH (0.632 g, 0.026 mole) was added slowly with magnetic stirring until the completion of hydrogen evolution. The capped bottle was removed from the drybox, and the solution was transferred to a 400 mL metal shaker tube in a nitrogen filled glovebag. The shaker tube was cooled to an internal temperature of −18° C., shaking was started, and perfluoropropylvinyl ether (PPVE, 77 g 0.289 mole) was added from a metal cylinder. The mixture was allowed to warm to room temperature and was shaken for 20 h. The entire reaction mixture was added to 600 mL water saturated with sodium chloride, and this mixture was extracted with 800 mL of methylene chloride in a separatory funnel. The methylene chloride layer was dried over MgSO$_4$, and concentrated in vacuo on a rotary evaporator to give a liquid (52.0 g) which was vacuum distilled in a Kugelrohr apparatus: first fraction 75° C. at 0.175 mm (11.0 g), second fraction 110° C. at 0.175 mm (35.7 g) $^1$H NMR of the first fraction showed a large amount of dimethylformamide so it was recombined with the material left in the distillation pot and redistilled to give 14.0 g of material with purity comparable to fraction 2. This redistilled fraction was combined with fraction 2, and $^1$H NMR (CDCl$_3$, ppm downfield of TMS) shows traces of DMF and 2-(Benzyloxy)ethanol starting material along with the desired product: 3.689, 4.125 (t, t, OCH$_2$CH$_2$O, 4.0H), 4.563 (s, OCH$_2$Ph, 2.0H), 5.879 (d, $^2J_{H-F}$=55 Hz, OCF$_2$CFHOC$_3$F$_7$, 1.0H), 7.333 (m, Ph).

A 400 mL metal shaker tube was charged with 2.0 g 10% Pd on carbon, 49.6 g of CF$_3$CF$_2$CF$_2$OCHFCF$_2$OCH$_2$CH$_2$OCH$_2$Ph prepared as described above, and 150 mL of ethanol. The tube was purged with nitrogen, closed, cooled to 15° C. internal temperature, evacuated, and pressurized to 100 psig (689.5×10$^3$ Pa) with hydrogen. The tube was heated and shaken and when it reached 60° C. the hydrogen pressure was increased to 400 psig (2758×10$^3$ Pa). Temperature and hydrogen pressure were maintained for 24 hours. The tube was cooled to room temperature, vented, and the reaction mixture was filtered through a pad of Celite to remove the Pd on carbon catalyst. The filtered solution was poured into 300 mL water, and the mixture was extracted three times with 100 mL diethyl ether. The combined ether extracts were dried over MgSO$_4$, and then concentrated on a rotary evaporator in vacuo to give 33.2 g colorless liquid. $^1$H NMR showed this material to be a mixture of the desired product C$_3$F$_7$OCFHCF$_2$CH$_2$CH$_2$OH and ethanol. It was washed twice with 100 mL water to remove the ethanol. Yield of the washed product was 26.4 g. $^1$H NMR (CDCl$_3$, ppm downfield from TMS): 2.296 (bs, —OH, 1.0H), 3.840, 4.095 (t, t, OCH$_2$CH$_2$O, 4.0H), 5.945 (d, $^2J_{H-F}$=51 Hz, OCF$_2$CFHOC$_3$F$_7$, 1.0H).

7) 2-[methyl[(3,3,4,4,5,5,6,6,7,7,8,8,8-tridecafluorooctyl)-sulfonyl]amino]ethyl ester of 2-propenoic acid is available from E. I. du Pont de Nemours and Company, Wilmington Del.

8) Hydrocarbon alcohols hexanol, heptanol, octanol, nonanol, decanol, and decylanol are available from Aldrich, St. Louis, Mo.

9) RHOPLEX 3829, formulation N-29-1 is available from Rohm & Haas, Philadelphia, Pa.

10) VISTA 6400 are paints having an acrylic semi-gloss resin with 84% gloss at 85 degrees available from Vista Paints, Fullerton, Calif.

11) C$_6$H$_{13}$CH$_2$CH$_2$SO$_2$N(CH$_3$)CH$_2$CH$_2$OH is available from E. I. du Pont de Nemours and Company, Wilmington, Del.

Test Method 1—Wetting and Leveling Test

To test the performance of the samples in their wetting and leveling ability, the samples were added to a floor polish (RHOPLEX 3829, Formulation N-29-1, available from Rohm & Haas, Philadelphia, Pa.]) and applied to half of a thoroughly cleaned 12 inch×12 inch (30.36 cm×30.36 cm) vinyl tile (available from Interfuse Vinyl Tiles by Estrie, Sherbrooke, QC Canada). The tiles are thoroughly cleaned by wetting the tiles, adding a powdered oxygen bleach cleanser and scrubbing using a green SCOTCH-BRITE scouring pad, available from 3M Company, St. Paul Min.). This scrubbing procedure was used to remove the pre-existing coating on the tiles. The tiles initially have a uniform shiny finish; a uniform dull finish indicates coating removal. The tiles are then air-dried overnight. A 1 wt % solution of the surfactant to be tested was prepared by dilution in deionized water. Following the resin manufacturer protocols, a 100 g portion of the RHOPLEX 3829 formulation was prepared, followed by addition of 0.75 g of the 1 wt % surfactant solution, to provide a test floor polish.

The test floor polish was applied to the tile by placing 3 mL portion of the test polish in the center of the tile, and spreading from top to bottom using a cheesecloth applicator, and finally placing a large "X" across the tile, using the applicator. The "X" subsequently provides visual evidence of leveling at the rating step. The applicator was prepared from a two-layer 18×36 inch (46×91 cm) sheet of cheesecloth (from VWR, West Chester Pa.), folded twice into an eight-layer pad. One corner of the pad was then used as the applicator. The tile was allowed to dry for 30 min. and a total of 5 coats (Coating #s 1-5) were applied and dried, with the X test performed after each coating had been dried. After each coat, the tile was rated on a 1 to 5 scale (1 being the worst, 5 the best) on the surfactant's ability to promote wetting and leveling of the polish on the tile surface. The rating is determined using the Tile Rating Scale below, based on comparison of a tile treated with the floor polish that contains no added surfactant.

TABLE 1

Visual Tile Rating Scale for Leveling

| Score | Description |
|---|---|
| 1 | Uneven surface coverage of the film, significant streaking and surface defects |
| 2 | Numerous surface defects and streaks are evident but, generally, film coats entire tile surface |
| 3 | Visible streaking and surface defects, withdrawal of the film from the edges of the tile |
| 4 | Minor surface imperfections or streaking |
| 5 | No visible surface defects or streaks |

Test Method 2—Surface Tension Measurement

Surface tension was measured according to the American Society for Testing and Materials ASTM # D1331-56, using the Wilhelmy plate method on a KRUSS K11 tensiometer (KRUSS USA, Matthews N.C.). Results are in mN/m (dynes/cm). The tensiometer was used according to the manufacturer's recommendations.

Test Method 3—Open-Time Extension

Open-time is time during which a layer of applied liquid coating composition can be blended into an adjacent layer of liquid coating composition without showing a lapmark, brush mark, or other application mark. It is also called wet-edge time. Low VOC latex paint has shorter than desired open-time due to lack of high boiling temperature VOC solvents. Lack of sufficient open-time will result in overlapping brush marks or other marks. Open-time testing is conducted by a well-accepted industry practice, called thumb press method as described herein. A double strip drawdown panel of the control sample and the sample with 0.1% active ingredient of the sample to be tested was employed. The coating composition to be tested and the control were the same coating composition wherein the control contained no additive to be tested, and the sample to be tested contained a composition of the present invention as an additive. The panel was made with a 7 cm doctor blade at 20-25° C. and 40-60% relative humidity. A double thumb press with equal pressure was then applied to each sample side by side at 1-2 minute intervals. The end point was when no paint residue on the thumb was observed. The time from when the drawdown was made to the end point was recorded as open-time. The percent difference between the control and sample containing the additive was recorded as the percent open-time extension. Compositions of the present invention were tested in a semi-gloss latex paint.

Test Method 4—Blocking Resistance of Architectural Latex Paints

The test method described herein is a modification of ASTM D4946-89, Standard Test Method for Blocking Resistance of Architectural Paints, which is hereby specifically incorporated by reference. The face-to-face blocking resistance of paints to be tested was evaluated in this test. Blocking, for the purpose of this test, is defined as the undesirable sticking together of two painted surfaces when pressed together or placed in contact with each other for an extended period of time.

The paint to be tested was cast on a polyester test panel using an applicator blade. All painted panels were protected from surface contamination, such as grease, oil, fingerprints, dust, and the like. Typically, results were sought at 24 hours after casting the paint. After the panels had been conditioned in a conditioned room with controlled temperature and humidity as specified in the test method for the desired period of time, six squares (3.8 cm×3.8 cm) were cut out from the painted test panel. The cut sections (three pairs) were placed with the paint surfaces face-to-face for each of the paints to be tested. The face-to-face specimens were placed in a 50° C. oven on a marble tray. A no. 8 stopper was placed on top, with the smaller diameter in contact with the specimens, and then a 1000 g weight was placed on top of the stopper. This resulted in a pressure of 1.8 psi (12,400 Pascal) on the specimens. One weight and stopper was used for each specimen tested. After exactly 30 minutes, the stoppers and weights were taken off the test specimens which were removed from the oven and allowed to cool in the conditioned room for 30 minutes before determining the resistance to blocking.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in the Table entitled Blocking Resistance Numerical Ratings below. The degree of seal was estimated from the appearance of the specimens and the fraction of the paint surfaces that adhere. Paint tearing away from the test panel backing was an indication of seal. A higher number indicated better resistance to blocking.

TABLE 2

Blocking Resistance Numerical Ratings

| Blocking Resistance Numerical Ratings | Description of the Separation | Performance Description |
|---|---|---|
| 10 | No tack | Perfect |
| 9 | Trace tack | Excellent |
| 8 | Very slight tack | Very good |
| 7 | Slight tack | Good/very good |
| 6 | Moderate to slight tack | Good |
| 5 | Moderate tack | Fair |
| 4 | Very tacky, no seal | Poor to Fair |
| 3 | 5-25% seal | Poor |
| 2 | 25-50% seal | Poor |
| 1 | 50-75% seal | Very poor |
| 0 | 75-100% seal | Very poor |

Test Method 5—Wickbold Torch Method (for Fluorine Analyses)

An efficient process for the quantitative mineralization of fluorinated compounds is the Wickbold torch combustion method. The method (described in detail in Angew Chem. 66 (1954) 173) was demonstrated to be compound independent for fluorine-containing compounds. In this process, the analytical sample was placed in a ceramic vessel and the sample, typically, was completely combusted by external heating in a vigorous oxygen stream. The gaseous reaction products wee passed through an auxiliary hydrogen/oxygen flame with excess oxygen, so the combustion became complete. The gaseous effluent was then condensed, and fluoride was solubilized in the aqueous stream which was collected for analy-

EXAMPLES

Examples 1-5

In a round-bottom 100-mL flask, equipped with a thermocouple and a magnetic stirrer bar, $POCl_3$ (0.58 g, 3.8 mmol) was dissolved in dry tetrahydrofuran (25 mL). The solution was cooled to 0° C. using an ice-bath. A separate solution containing the fluorinated alcohol $C_3F_7OCFHCF_2CH_2CH_2OH$ (1.25 g, 3.8 mmol) prepared as disclosed under Materials, and triethylamine (0.96 g, 9.5 mmol) in dry tetrahydrofuran (15 mL) was then slowly added to the reactor. The reaction was allowed to proceed for 1-2 h at 0° C. A solution of hydrocarbon alcohol in the amount listed in Table 3 in dry tetrahydrofuran (15 mL) was slowly added to the reaction mass. The reaction mass was stirred overnight at ambient temperature. The solids were then filtered and the solvent evaporated using a ROTOVAP (Heidolph LABOROTA 4000 Efficient, Schwabach, Germany). The resulting oil was diluted in tetrahydrofuran (10 mL) and a solution of NaOH (0.34 g, 8.6 mmol) dissolved in water (1 mL) was added to the reaction mass. The mixture was stirred overnight at room temperature. The solvent was then evaporated using a ROTOVAP, the resulting solids were washed with chloroform (50 mL), and filtered. The final product was dried overnight at 120° C. and 150 mmHg (20 kPa) in a vacuum oven. The products obtained were compounds of Formula 1 wherein $R_f$ is $C_3F_7$, A is $OCFHCF_2OE$, E is $CH_2CH_2OH$, M is Na, and $R_H$ is $C_6H_{13}$ for Example 1, $C_7H_{15}$ for Example 2, $C_8H_{17}$ for Example 3, $C_9H_{19}$ for Example 4 and $C_{10}H_{21}$ for Example 5. Each product was tested for surface tension using Test Method 2. The results are listed in Table 5.

Comparative Example A

The process of Examples 1-5 was employed using two mole equivalents of the fluorinated alcohol and no hydrocarbon alcohol. Comparative Example A is a compound similar to Formula 1 but having a second $R_f$ in place of the $R_H$, wherein $R_f$ is $C_3F_7$, A is $OCFHCF_2OE$, E is $CH_2CH_2OH$, M is Na, and the second $R_f$ is $C_3F_7$. This Comparative Example was tested for surface tension using Test Method 2. The results are listed in Table 5.

The fluoroalcohol compositions used in the Examples and referenced in Table 4 are shown in Table 3 below.

TABLE 3

| Table 3 Designation | Alcohol |
|---|---|
| I | $C_4H_9CH_2CF_2CH_2CH_2OH$ |
| II | $C_4F_9(CH_2CF_2)_2CH_2CH_2OH$ |
| III | $C_6F_{13}CH_2CF_2CH_2CH_2OH$ |
| IV | $C_6F_{13}(CH_2CF_2)_2CH_2CH_2OH$ |
| V | $C_3F_7OCF_2CF_2CH_2CH_2OH$ |
| VI | $C_3F_7OCFHCF_2CH_2CH_2OH$ |
| VII | $C_6H_{13}CH_2CH_2SO_2N(CH_3)CH_2$—$CH_2OH$ |

Fluorinated Alcohols

TABLE 4

Synthesis of Hybrid Phosphate Surfactants

| Example | Phosphorous oxychloride Amount, g | mmol. | Triethylamine Amount, g | mmol. | Fluorinated alcohol Name (See Table 2) | Amount, g | mmol. | Hydrocarbon alcohol Name | Amount, g | mmol. | Average % Yield |
|---|---|---|---|---|---|---|---|---|---|---|---|
| Comp. A | 0.58 | 3.8 | 0.96 | 9.5 | VI | 2.5 | 7.6 | n/a | 0.00 | 0 | 82.5 |
| 1 | 0.58 | 3.8 | 0.96 | 9.5 | VI | 1.25 | 3.8 | Hexanol | 0.39 | 3.8 | 81.5 |
| 2 | 0.58 | 3.8 | 0.96 | 9.5 | VI | 1.25 | 3.8 | Heptanol | 0.44 | 3.8 | 74 |
| 3 | 0.58 | 3.8 | 0.96 | 9.5 | VI | 1.25 | 3.8 | Octanol | 0.49 | 3.8 | 86 |
| 4 | 0.58 | 3.8 | 0.96 | 9.5 | VI | 1.25 | 3.8 | Nonanol | 0.55 | 3.8 | 89 |
| 5 | 0.58 | 3.8 | 0.96 | 9.5 | VI | 1.25 | 3.8 | Decylanol | 0.60 | 3.8 | 96 |
| Comp. B | 1.3 | 8.6 | 2.1 | 21 | I | 5.64 | 17.2 | n/a | 0.00 | 0 | 82 |
| 6 | 0.58 | 3.8 | 0.96 | 9.5 | I | 1.25 | 3.8 | Hexanol | 0.39 | 3.8 | 53 |
| 7 | 0.58 | 3.8 | 0.96 | 9.5 | I | 1.25 | 3.8 | Heptanol | 0.44 | 3.8 | 55 |
| 8 | 1.3 | 8.6 | 2.1 | 21 | I | 2.82 | 8.6 | Octanol | 1.10 | 8.6 | 82 |
| 9 | 0.58 | 3.8 | 0.96 | 9.5 | I | 1.25 | 3.8 | Nonanol | 0.55 | 3.8 | 76.6 |
| 10 | 0.58 | 3.8 | 0.96 | 9.5 | I | 1.25 | 3.8 | Decylanol | 0.60 | 3.8 | 73 |
| Comp. C | 1.3 | 8.6 | 2.1 | 21 | V | 5.68 | 17.2 | n/a | 0.00 | 0 | 77.3 |
| 11 | 0.58 | 3.8 | 0.96 | 9.5 | V | 1.5 | 3.8 | Hexanol | 0.39 | 3.8 | 71 |
| 12 | 0.58 | 3.8 | 0.96 | 9.5 | V | 1.5 | 3.8 | Heptanol | 0.44 | 3.8 | 66.7 |
| 13 | 1.3 | 8.6 | 2.1 | 21 | V | 2.83 | 8.6 | Octanol | 1.10 | 8.6 | 91 |
| 14 | 0.58 | 3.8 | 0.96 | 9.5 | V | 1.5 | 3.8 | Nonanol | 0.55 | 3.8 | 90 |
| 15 | 0.58 | 3.8 | 0.96 | 9.5 | V | 1.5 | 3.8 | Decanol | 0.60 | 3.8 | 83 |
| Comp. D | 1.3 | 8.6 | 2.1 | 21 | II | 6.74 | 17.2 | n/a | 0.00 | 0 | 71 |
| 16 | 0.58 | 3.8 | 0.96 | 9.5 | II | 1.49 | 3.8 | Hexanol | 0.39 | 3.8 | 54.2 |
| 17 | 0.58 | 3.8 | 0.96 | 9.5 | II | 1.49 | 3.8 | Heptanol | 0.44 | 3.8 | 79 |
| 18 | 1.3 | 8.6 | 2.1 | 21 | II | 3.37 | 8.6 | Octanol | 1.10 | 8.6 | 71 |
| 19 | 0.58 | 3.8 | 0.96 | 9.5 | II | 1.49 | 3.8 | Nonanol | 0.55 | 3.8 | 83.8 |
| 20 | 0.58 | 3.8 | 0.96 | 9.5 | II | 1.49 | 3.8 | Decanol | 0.60 | 3.8 | 82 |
| Comp. E | 1.3 | 8.6 | 2.1 | 21 | III | 7.36 | 17.2 | n/a | 0.00 | 0 | 73 |
| 21 | 1.3 | 8.6 | 2.1 | 21 | III | 3.68 | 8.6 | Octanol | 1.10 | 8.6 | 53 |
| Comp. F | 1.3 | 8.6 | 2.1 | 21 | IV | 8.46 | 17.2 | n/a | 0.00 | 0 | 66 |
| 22 | 1.3 | 8.6 | 2.1 | 21 | IV | 4.23 | 8.6 | Octanol | 1.10 | 8.6 | 58 |
| Comp. G | 1.3 | 8.6 | 2.1 | 21 | VII | 8.35 | 17.2 | n/a | 0.00 | 0 | 26 |
| 23 | 1.3 | 8.6 | 2.1 | 21 | VII | 4.2 | 8.6 | Octanol | 1.10 | 8.6 | 31 |

TABLE 5

Surface Tension Results for Hybrid Surfactants

| | | Concentration, % by weight | | |
|---|---|---|---|---|
| | | 0.5 | 0.1 | 0.05 |
| Example | % F* | Surface Tension by Test Method 2 (mN/m) | | |
| Comparative A | 42.6 | 15.1 | 16.4 | 18.5 |
| 1 | 30.6 | 15.7 | 20.5 | 26.0 |
| 2 | 29.0 | 15.8 | 19.6 | 25.5 |
| 3 | 27.2 | 16.2 | 17.4 | 22.7 |
| 4 | 28.0 | 16.8 | 17.5 | 20.3 |
| 5 | 26.5 | 17.1 | 17.6 | 18.6 |

*Calculated value from the stoichiometry of the reaction.

Table 5 shows the surface tension of Examples 1 to 5. Their performance was tested against the non-hybrid Comparative Example A which contained a higher level of fluorine. Examples 1 to 5 showed surface tension of less than about 25 mN/m, and often less than 20 mN/m, at low concentrations of less than 0.5% by weight in water, and thus demonstrated excellence performance as surfactants. Examples 4, 5 and Comparative Example A each reduced surface tension to less than 20 mN/m at a concentration of 0.05% by weight in water. At this concentration of 0.05% by weight of surfactant in water, the fluorine content was diluted to 0.024 for Comparative Example A and to 0.014% and 0.013% for Examples 4 and 5 respectively. Therefore Examples 4 and 5 were more fluorine efficient even at this very low concentration.

Examples 6-10

The procedure of Examples 1-5 was employed using $C_4F_9CH_2CF_2CH_2CH_2OH$ as the fluorinated alcohol in the amount listed in Table 3, and using the hydrocarbon alcohols in the amount listed in Table 3. The products obtained were compounds of Formula 1 wherein $R_f$ is $C_4F_9$, A is $CH_2CF_2CH_2CH_2$, M is Na, and $R_H$ is $C_6H_{13}$ for Example 6, $C_7H_{15}$ for Example 7, $C_8H_{17}$ for Example 8, $C_9H_{19}$ for Example 9 and $C_{10}H_{21}$ for Example 10. Each product was tested for surface tension using Test Method 2. The results are listed in Table 6.

Comparative Example B

The process of Examples 6-10 was employed using two mole equivalents of the fluorinated alcohol and no hydrocarbon alcohol. Comparative Example B is a compound similar to Formula 1 but having a second $R_f$ in place of the $R_H$, wherein $R_f$ is $C_4F_9$, A is $CH_2CF_2CH_2CH_2$, M is Na, and the second $R_f$ is $C_4F_9$. The product was tested for surface tension using Test Method 2. The results are listed in Table 6.

TABLE 6

Surface Tension (Dynes/cm) for Hybrid Surfactants

| | | Concentration, % wt. | | |
|---|---|---|---|---|
| | | 0.5 | 0.1 | 0.05 |
| Example | % F* | Surface Tension by Test Method 2 (mN/m) | | |
| Comp. B | 52.0 | 15.7 | 15.9 | 19.7 |
| 6 | 36.2 | 17.1 | 25.6 | 29.9 |
| 7 | 35.2 | 16.2 | 17.4 | 20.4 |
| 8 | 34.4 | 17.5 | 18.5 | 25.3 |

TABLE 6-continued

Surface Tension (Dynes/cm) for Hybrid Surfactants

| | | Concentration, % wt. | | |
|---|---|---|---|---|
| | | 0.5 | 0.1 | 0.05 |
| Example | % F* | Surface Tension by Test Method 2 (mN/m) | | |
| 9 | 33.6 | 17.4 | 25.0 | 30.9 |
| 10 | 32.9 | 17.7 | 18.8 | 22.5 |

*Calculated value from the stoichiometry of the reaction.

Table 6 shows the surface tension results for Examples 6-10. Their performance was tested against the non-hybrid Comparative Example B which contained a higher level of fluorine. Generally Examples 6-10 demonstrated excellent surfactant properties at low concentrations in water, achieving a surface tension of less than about 30 mN/m at a concentration of 0.05% by weight, and less than 20 mN/m at a concentration of 0.5% by weight. The best performance was obtained for Example 7, which was prepared using 1-heptanol as the hydrocarbon alcohol. Both Example 7 and Comparative Example B lowered the surface tension of water to 20 mN/m or below at 0.05% by weight surfactant concentration. However, at this concentration Example 7 contained only 0.018% by weight fluorine while Comparative Example B contained 0.026% by weight fluorine to get similar surface effects, thus demonstrating greater fluorine efficiency for Example 7.

Examples 11-15

The procedure of Examples 1-5 was employed using $C_3F_7OCF_2CF_2CH_2CH_2OH$ as the fluorinated alcohol in the amount listed in Table 3, and using the hydrocarbon alcohols in the amount listed in Table 3. The products obtained were compounds of Formula 1 wherein $R_f$ is $C_3F_7$, A is $OCF_2CF_2CH_2CH_2$, M is Na, and $R_H$ is $C_6H_{13}$ for Example 11, $C_7H_{15}$ for Example 12, $C_8H_{17}$ for Example 13, $C_9H_{19}$ for Example 14 and $C_{10}H_{21}$ for Example 15. Each product was tested for surface tension using Test Method 2. The results are listed in Table 7.

Comparative Example C

The process of Examples 11-15 was employed using two mole equivalents of the fluorinated alcohol and no hydrocarbon alcohol. Comparative Example C is a compound similar to Formula 1 but having a second $R_f$ in place of the $R_H$, wherein $R_f$ is $C_3F_7$, A is $OCF_2CF_2CH_2CH_2$, M is Na, and the second $R_f$ is $C_3F_7$. The product was tested for surface tension using Test Method 2. The results are listed in Table 7.

TABLE 7

Surface Tension Results for Hybrid Surfactants

| | | Concentration, % wt. | | |
|---|---|---|---|---|
| | | 0.5 | 0.1 | 0.05 |
| Example | % F | Surface Tension by Test Method 2 (mN/m) | | |
| Comp. C | 49.5 | 15.3 | 15.8 | 16.0 |
| 11 | 37.0 | 18.5 | 18.9 | 20.4 |
| 12 | 36.5 | 15.5 | 16.6 | 20.7 |

TABLE 7-continued

Surface Tension Results for Hybrid Surfactants

| Example | % F | Concentration, % wt. | | |
|---|---|---|---|---|
| | | 0.5 | 0.1 | 0.05 |
| | | Surface Tension by Test Method 2 (mN/m) | | |
| 13 | 35.5 | 16.4 | 16.7 | 18.4 |
| 14 | 34.9 | 16.6 | 17.1 | 17.2 |
| 15 | 34.3 | 17.4 | 18.1 | 17.8 |

*Measured by Torch Method, Test Method 5.

Table 7 shows the surface tension results for Examples 11-15. Their performance is compared against the non-hybrid Comparative Example C which contained a higher level of fluorine. All the hybrid surfactants of Examples 11 to 15 demonstrated excellent performance as surfactants by lowering the surface tension of water to about 20 mN/m or less at 0.05% by weight of active ingredient. The performance was comparable to Comparative Example C despite the lower level of fluorine in Examples 11-15. All the hybrid surfactants of Examples 11-15 as shown on Table 7 demonstrated better fluorine efficiency than the Comparative Example C. At a concentration of 0.05% by weight in water, Examples 11-15 and Comparative Example C each achieved a surface tension of about 20 mN/m or less, but at this diluted concentration Comparative Example C contained 0.025% fluorine, while Examples 11-15 contained 0.017 to 0.019% fluorine.

Examples 16-20

The procedure of Examples 1-5 was employed using $C_4F_9(CH_2CF_2)_2CH_2CH_2OH$ as the fluorinated alcohol in the amount listed in Table 3, and using the hydrocarbon alcohols in the amount listed in Table 3. The products obtained were compounds of Formula 1 wherein $R_f$ is $C_4F_9$, A is $(CH_2CF_2)_2CH_2CH_2$, M is Na, and $R_H$ is $C_6H_{13}$ for Example 16, $C_7H_{15}$ for Example 17, $C_8H_{17}$ for Example 18, $C_9H_{19}$ for Example 19 and $C_{10}H_{21}$ for Example 20. Each product was tested for surface tension using Test Method 2. The results are listed in Table 8.

Comparative Example D

The process of Examples 16-20 was employed using two mole equivalents of the fluorinated alcohol and no hydrocarbon alcohol. Comparative Example D is a compound similar to Formula 1 but having a second $R_f$ in place of the $R_H$, wherein $R_f$ is $C_4F_9$, A is $(CH_2CF_2)_2CH_2CH_2$, M is Na, and the second $R_f$ is $C_4F_9$. The product was tested for surface tension using Test Method 2. The results are listed in Table 8.

TABLE 8

Surface Tension Results for Hybrid Surfactants

| Example | % F | Concentration, % wt. | | |
|---|---|---|---|---|
| | | 0.5 | 0.1 | 0.05 |
| | | Surface Tension by Test Method 2 (mN/m) | | |
| Comp. D | 52.8 | 15.7 | 16.7 | 16.8 |
| 16 | 38.4 | 17.3 | 18.4 | 22.6 |
| 17 | 37.5 | 16.5 | 19.0 | 21.7 |
| 18 | 36.7 | 16.9 | 17.6 | 18.3 |

TABLE 8-continued

Surface Tension Results for Hybrid Surfactants

| Example | % F | Concentration, % wt. | | |
|---|---|---|---|---|
| | | 0.5 | 0.1 | 0.05 |
| | | Surface Tension by Test Method 2 (mN/m) | | |
| 19 | 35.8 | 17.1 | 17.5 | 17.8 |
| 20 | 35.2 | 17.5 | 17.8 | 17.9 |

*Calculated value from the stoichiometry of the reaction.

Table 8 compares the surface tension data obtained for Examples 16-20 against the non-hybrid Comparative Example D which contained a higher level of fluorine. Examples 16-20 had similar surface tension profiles as Comparative Example D, but achieved these results with less fluorine present in the compounds. All of Examples 16-20 demonstrated excellent surface tension reduction in water at low concentrations, achieving a surface tension of less than about 20 mN/m at a concentration of 0.05% by weight in water.

Example 21

The procedure of Examples 1-5 was employed using $C_6F_{13}CH_2CF_2CH_2CH_2OH$ as the fluorinated alcohol in the amount listed in Table 3, and using octanol as the hydrocarbon alcohol in the amount listed in Table 3. The product obtained was a compound of Formula 1 wherein $R_f$ is $C_6F_{13}$, A is $CH_2CF_2CH_2CH_2$, M is Na, and $R_H$ is $C_8H_{17}$. The product was tested for surface tension using Test Method 2. The results are listed in Table 9.

Comparative Example E

The process of Example 21 was employed using two mole equivalents of the fluorinated alcohol and no hydrocarbon alcohol. Comparative Example E is a compound similar to Formula 1 but having a second $R_f$ in place of the $R_H$, wherein $R_f$ is $C_6F_{13}$, A is $CH_2CF_2CH_2CH_2$, M is Na, and the second $R_f$ is $C_6F_{13}$. The product was tested for surface tension using Test Method 2. The results are listed in Table 9.

TABLE 9

Surface Tension Results for Hybrid Surfactants

| Example | % F | Concentration, % wt. | | | |
|---|---|---|---|---|---|
| | | 0.5 | 0.1 | 0.05 | 0.01 |
| | | Surface Tension by Test Method 2 (mN/m) | | | |
| Comparative E | 53.2 ± 0.8 | 33.8 ± 0.6 | 39.9 ± 1.0 | 45.3 ± 0.6 | 50.1 ± 4.2 |
| 21 | 39.7 ± 0.5 | 16.5 ± 1.0 | 17.6 ± 1.4 | 18.3 ± 1.4 | 25.5 ± 1.6 |

*Calculated value from the stoichiometry of the reaction.

Table 9 compares the surface tension results for the hybrid surfactant of Example 21 against the Comparative Example E. Example 21 reduced the surface tension of water to less than 20 mN/m at 0.05% by weight of surfactant while containing less fluorine than Comparative Example E. The integration of the hydrocarbon and fluorocarbon segments into the phosphate surfactant significantly improved its surface effects and enhanced fluorine efficiency.

Example 22

The procedure of Examples 1-5 was employed using $C_6F_{13}(CH_2CF_2)_2CH_2CH_2OH$ as the fluorinated alcohol in the amount listed in Table 3, and using octanol as the hydrocarbon alcohol in the amount listed in Table 3. The product obtained was a compound of Formula 1 wherein $R_f$ is $C_6F_{13}$, A is $(CH_2CF_2)_2CH_2CH_2$, M is Na, and $R_H$ is $C_8H_{17}$. The product was tested for surface tension using Test Method 2. The results are listed in Table 10.

Comparative Example F

The process of Example 22 was employed using two mole equivalents of the fluorinated alcohol and no hydrocarbon alcohol. Comparative Example F is a compound similar to Formula 1 but having a second $R_f$ in place of the $R_H$, wherein $R_f$ is $C_6F_{13}$, A is $(CH_2CF_2)_2CH_2CH_2$, M is Na, and the second $R_f$ is $C_6F_{13}$. The product was tested for surface tension using Test Method 2. The results are listed in Table 10.

TABLE 10

Surface Tension Results for Hybrid Surfactants

| | | Concentration, % wt. | | | | |
|---|---|---|---|---|---|---|
| | | 0.5 | 0.1 | 0.05 | 0.01 | 0.005 |
| Example | % F | Surface Tension by Test Method 2 (mN/m) | | | | |
| Comparative F | 52.9 ± 2.4 | 31.8 ± 2.6 | 38.8 ± 3.6 | 48.0 ± 6.1 | 55.0 ± 10.4 | 58.6 ± 8.8 |
| 22 | 33.7 ± 1.2 | 17.0 ± 0.3 | 17.2 ± 0.2 | 17.2 ± 0.2 | 19.4 ± 0.6 | 23.8 ± 0.5 |

*Calculated value from the stoichiometry of the reaction.

Table 10 presents the surface tension data for the hybrid surfactant Example 22 and Comparative Example F. Comparative Example F was a non-hybrid surfactant containing a higher level of fluorine than Example 22. Example 22 produced excellent performance. This hybrid material was capable of reducing the surface tension of water to less than 25 mN/m at a concentration of 0.005% by weight of surfactant, and to less than 20 mN/m at 0.01% by weight of surfactant. The incorporation of the 1-octanol group hydrocarbon group into the fluorinated phosphate produced a dramatic enhancement in surface effects and fluorine efficiency.

Example 23

The procedure of Examples 1-5 was employed using $C_6F_{13}CH_2CH_2SO_2$—$N(CH_3)$ $CH_2CH_2OH$ as the fluorinated alcohol in the amount listed in Table 3, and using octanol as the hydrocarbon alcohol in the amount listed in Table 3. The product obtained was a compound of Formula 1 wherein $R_f$ is $C_6F_{13}$, A is $CH_2CH_2N(CH_3)SO_2CH_2CH_2$, M is Na, and $R_H$ is $C_8H_{17}$. The product was tested for surface tension using Test Method 2. The results are listed in Table 11.

Comparative Example G

The process of Example 23 was employed using two mole equivalents of the fluorinated alcohol and no hydrocarbon alcohol. Comparative Example F is a compound similar to Formula 1 but having a second $R_f$ in place of the $R_H$, wherein $R_f$ is $C_6F_{13}$, A is $CH_2CH_2N(CH_3)SO_2CH_2CH_2$, M is Na, and $R_H$ is $C_6F_{13}$. The product was tested for surface tension using Test Method 2. The results are listed in Table 11.

TABLE 11

Surface Tension Results for Hybrid Surfactants

| | | Concentration, % wt. | | | |
|---|---|---|---|---|---|
| | | 0.5 | 0.1 | 0.05 | 0.01 |
| Example | % F | Surface Tension by Test Method 2 (mN/m) | | | |
| Comparative G | 44.1 | 32.1 ± 4.7 | 39.3 ± 7.1 | 46.4 ± 7.6 | 55.5 ± 5.1 |
| 23 | 32.4 | 17.5 ± 0.4 | 18.7 ± 0.3 | 19.5 ± 0.2 | 25.9 ± 1.4 |

*Calculated value from the stoichiometry of the reaction.

Table 11 shows the surface tension data for hybrid surfactant Example 23 and Comparative Example G which contained a higher level of fluorine. Example 23, containing less fluorine than Comparative Example G, produced excellent performance. This hybrid material of Example 23 was capable of reducing the surface tension of water to less than 20 dynes/cm (mN/m) at 0.05% by weight of surfactant. Example 23 demonstrated improved fluorine efficiency and much better surface effects than the Comparative Example G.

Testing in Paint

Examples 8 and 18, and Comparative Examples B and D, each prepared as described above, were added to each of Vista 6400 paints in an amount to provide 70 ppm (micrograms per gram) fluorine in 100 g of paint. Paint with no additive was used as a control (blank). The paint was applied to polyester test panels and tested for blocking in accordance with Test Method 4 and open time extension using Test Method 3. The resulting data is shown in Tables 12 and 13.

TABLE 12

Blocking Results

| Paint | Example as Additive | Fluorine, ppm | Average Blocking Score* |
|---|---|---|---|
| Vista 6400 | None (Blank) | 0 | 0 |
| Vista 6400 | Comp. B | 70 | 6.3 |
| Vista 6400 | 8 | 70 | 6.7 |
| Vista 6400 | Comp. D | 70 | 6.0 |
| Vista 6400 | 18 | 70 | 3.7 |

*By Test Method 4.

The blocking test results for Examples 8 and 18 are presented in Table 12. Their performance was compared against a blank and against Comparative Examples B and D. Example 8 demonstrated excellent blocking performance by outperforming both the blank and Comparative Example B. Example 18 showed better blocking performance than the blank but not superior to the Comparative Example D. Overall, the best blocking effect is produced by Example 8, which has a blocking score of 6.7.

TABLE 13

Open-Time Extension

| Paint | Additive | Fluorine, ppm | % Open time extension* |
|---|---|---|---|
| Vista 6200 | Comp. Ex. B | 500 | 4.4 |
| Vista 6200 | 8 | 500 | 4.4 |
| Vista 6200 | Comp. Ex. D | 500 | 2.2 |
| Vista 6200 | 18 | 500 | 7.0 |

*By Test Method 3.

Table 13 shows the results for the open-time extension test using Examples 8 and 18. The performances of these Examples were evaluated against Comparative Examples B and D. Example 8 produced open time extension equivalent to that of Comparative Example B at equal fluorine dose. On the other hand, Example 18 exhibited open time extension that was superior to that for Comparative Example D. These results demonstrate that the hybrid surfactants in Examples 8 and 18 are capable of providing equal or better performance than the non-hybrid Comparative Examples B and D.

What is claimed is:

1. A compound of Formula 1

$$R_f\text{-A-OP(O)(O}^-M^+)(O-R_H) \quad \text{Formula 1}$$

wherein
$R_f$ is a $C_2$ to $C_6$ linear or branched perfluoroalkyl optionally interrupted by one, two or three ether oxygen atoms;
A is $(CH_2CF_2)_m(CH_2)_n-$, $(CH_2)_oSO_2N(CH_3)(CH^2)_p-$, $O(CF_2)_q(CH_2)_r-$, or $OCHFCF_2OE-$;
m is 1 to 4; n, o, p, and r are each independently 2 to 20; q is 2;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
M is a Group I metal or an ammonium cation $(NH_xR^2_y)^+$ wherein $R^2$ is a $C_1$ to $C_4$ alkyl, x is 1 to 4, y is 0 to 3 and x+y is 4; and
$R_H$ is a $C_1$ to $C_{20}$ linear, branched, or cyclic alkyl;
wherein the compound of Formula 1 is a surfactant for aqueous, halocarbon, or hydrocarbon liquid medium.

2. The compound of claim 1 wherein $R_f$ is a $C_3$ to $C_6$ linear or branched perfluoroalkyl.

3. The compound of claim 1 wherein A is $(CH_2CF_2)_m(CH_2)_n-$, n is 2, and $R_f$ is $C_4$ perfluoroalkyl or $C_6$ perfluoroalkyl.

4. The compound of claim 3 wherein $R_H$ is $C_8H_{17}$.

5. The compound of claim 1 wherein A is $(CH_2)_oSO_2N(CH_3)(CH_2)_p-$, o and p are each 2, $R_f$ is $C_6$ perfluoroalkyl and $R_H$ is $C_8H_{17}$.

6. The compound of claim 1 wherein A is $O(CF_2)_q(CH_2)_r-$, q and r are each 2, $R_f$ is $C_3F_7$ and $R_H$ is $C_8H_{17}$.

7. The compound of claim 1 wherein A is $OCHFCF_2OE-$, $R_f$ is $C_3F_7$ and $R_H$ is $C_8H_{17}$.

8. The compound of claim 1 having a surface tension of about 25 mN/m or less at a concentration of 0.1% by weight in water.

9. The compound of claim 1 having a surface tension of about 20 mN/m or less at a concentration of 0.5% by weight in water.

10. A method of lowering the surface tension of an aqueous medium comprising contacting the medium with a composition of Formula 1

$$R_f\text{-A-OP(O)(O}^-M^+)(O-R_H) \quad \text{Formula 1}$$

wherein
$R_f$ is a $C_2$ to $C_6$ linear or branched perfluoroalkyl optionally interrupted by one, two or three ether oxygen atoms;
A is $(CH_2CF_2)_m(CH_2)_n-$, $(CH_2)_oSO_2N(CH_3)(CH^2)_p-$, $O(CF_2)_q(CH_2)_r-$, or $OCHFCF_2OE-$;
m is 1 to 4; n, o, p, and r are each independently 2 to 20; q is 2;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
M is a Group I metal or an ammonium cation $(NH_xR^2_y)^+$ wherein $R^2$ is a $C_1$ to $C_4$ alkyl, x is 1 to 4, y is 0 to 3 and x+y is 4; and
$R_H$ is a $C_1$ to $C_{20}$ linear, branched, or cyclic alkyl;
wherein the compound of Formula 1 is a surfactant for aqueous, halocarbon, or hydrocarbon liquid medium.

11. The method of claim 10 wherein the medium is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent.

12. The method of claim 10 wherein the compound of Formula 1 is applied to a substrate prior to contacting with the medium.

13. A method of providing leveling, open time extension, and resistance to blocking to a coated substrate comprising adding to a coating base prior to deposition on the substrate a compound of Formula 1

$$R_f\text{-A-OP(O)(O}^-M^+)(O-R_H) \quad \text{Formula 1}$$

wherein
$R_f$ is a $C_2$ to $C_6$ linear or branched perfluoroalkyl optionally interrupted by one, two or three ether oxygen atoms;
A is $(CH_2CF_2)_m(CH_2)_n-$, $(CH_2)_oSO_2N(CH_3)(CH^2)_p-$, $O(CF_2)_q(CH_2)_r-$, or $OCHFCF_2OE-$;
m is 1 to 4; n, o, p, and r are each independently 2 to 20; q is 2;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
M is a Group I metal or an ammonium cation $(NH_xR^2_y)^+$ wherein $R^2$ is a $C_1$ to $C_4$ alkyl, x is 1 to 4, y is 0 to 3 and x+y is 4; and
$R_H$ is a $C_1$ to $C_{20}$ linear, branched, or cyclic alkyl;
wherein the compound of Formula 1 is a surfactant for aqueous, halocarbon, or hydrocarbon liquid medium.

14. The method of claim 13 wherein the coating base is a water dispersed coating, alkyd coating, Type I urethane coating, unsaturated polyester coating, or a floor polish.

* * * * *